(12) United States Patent
Puente et al.

(10) Patent No.: US 7,036,985 B2
(45) Date of Patent: May 2, 2006

(54) X-RAY POSITIONING DEVICE

(75) Inventors: Carlos G. Puente, Santa Fe (AR); Alejandro Jaime, La Paz-Entre Rios (AR)

(73) Assignee: Ultradent Products, Inc., South Jordan, UT (US)

( * ) Notice: Subject to any disclaimer, the term of this patent is extended or adjusted under 35 U.S.C. 154(b) by 148 days.

(21) Appl. No.: 10/786,193

(22) Filed: Feb. 25, 2004

(65) Prior Publication Data

US 2005/0185767 A1 Aug. 25, 2005

(51) Int. Cl.
*A61B 6/14* (2006.01)

(52) U.S. Cl. ...................................... 378/170; 378/191

(58) Field of Classification Search ........ 378/168–170, 378/191
See application file for complete search history.

(56) References Cited

U.S. PATENT DOCUMENTS

| | | | | |
|---|---|---|---|---|
| 2,090,933 A | * | 8/1937 | Bolin | 378/170 |
| 3,092,721 A | | 6/1963 | Medwedeff et al. | 250/70 |
| 3,473,026 A | | 10/1969 | Updegrave | 250/70 |
| 4,365,162 A | | 12/1982 | Jarby | 378/170 |
| 4,554,676 A | * | 11/1985 | Maldonado et al. | 378/170 |
| 4,707,847 A | * | 11/1987 | Van Aken | 378/170 |
| 4,815,117 A | | 3/1989 | Waldo | 378/168 |
| 4,866,750 A | | 9/1989 | Chavarria et al. | 378/168 |
| 4,907,251 A | * | 3/1990 | Mork et al. | 378/39 |
| 4,965,885 A | | 10/1990 | Fuhrmann | 378/168 |
| 5,044,009 A | * | 8/1991 | Klauser | 378/170 |
| 5,090,047 A | * | 2/1992 | Angotti et al. | 378/170 |
| 5,119,410 A | * | 6/1992 | Donato | 378/170 |
| 5,289,522 A | | 2/1994 | Kanbar et al. | 378/170 |
| 5,327,477 A | * | 7/1994 | Levy | 378/168 |
| 5,652,779 A | | 7/1997 | Levy et al. | 378/170 |
| 5,708,696 A | | 1/1998 | Kantor | 378/206 |
| 5,799,058 A | * | 8/1998 | Willis et al. | 378/168 |
| 6,012,841 A | | 1/2000 | Slaughter | 378/170 |
| 6,033,111 A | | 3/2000 | Winters et al. | 378/170 |
| 6,190,042 B1 | | 2/2001 | Dove et al. | 378/170 |
| 6,343,875 B1 | | 2/2002 | Eppinger et al. | 378/170 |
| 6,424,694 B1 | | 7/2002 | Molteni et al. | 378/38 |
| 6,540,399 B1 | | 4/2003 | Eppinger et al. | 378/170 |
| 6,905,244 B1 | * | 6/2005 | Kilcher et al. | 378/170 |
| 6,932,505 B1 | * | 8/2005 | Yao et al. | 378/170 |
| 2002/0076002 A1 | | 6/2002 | Eppinger et al. | |
| 2002/0176539 A1 | | 11/2002 | Da Rold et al. | |
| 2002/0196903 A1 | | 12/2002 | Eppinger et al. | |

(Continued)

OTHER PUBLICATIONS

"A Universal Film Holding-Beam Alignment System for Paralleling, Bisecting Angle and Endodontic Radiography" Assembly Instructions by Dunvale Snapex System.

(Continued)

*Primary Examiner*—Craig E. Church
*Assistant Examiner*—Thomas R Artman
(74) *Attorney, Agent, or Firm*—Workman Nydegger

(57) ABSTRACT

An x-ray positioning device that allows a dental practitioner to adjust the x-ray beam horizontally and vertically relative to the center of the radiographic film with a great degree of precision. The device includes a frame, a bite block connected to the frame, an aiming ring connected to the frame, and an image receptor holder that is also connected to the frame. The aiming ring and image receptor holder are adjustable so as to allow the x-ray beam directed through the aiming ring to be adjustable horizontally and vertically relative to the center of an image receptor (e.g. a radiographic film packet) retained by the image receptor holder.

13 Claims, 5 Drawing Sheets

U.S. PATENT DOCUMENTS

2003/0058988 A1    3/2003    Molteni et al.

OTHER PUBLICATIONS

Cohn, Steven, A., D.D.S., "Principles and Clinical Techniques." Endodontic Radiography. 1988.

XCP Positioning Instructions for XCP Kit Evolution 2000 with Bite-wing Holder. XCP Kit without Bite-Wing Holder. XCP Instruction Poster.

"Intraoral Radiography With Rinn XCP/BAI Instructions" Rinn Corporation 1967-1989.

* cited by examiner

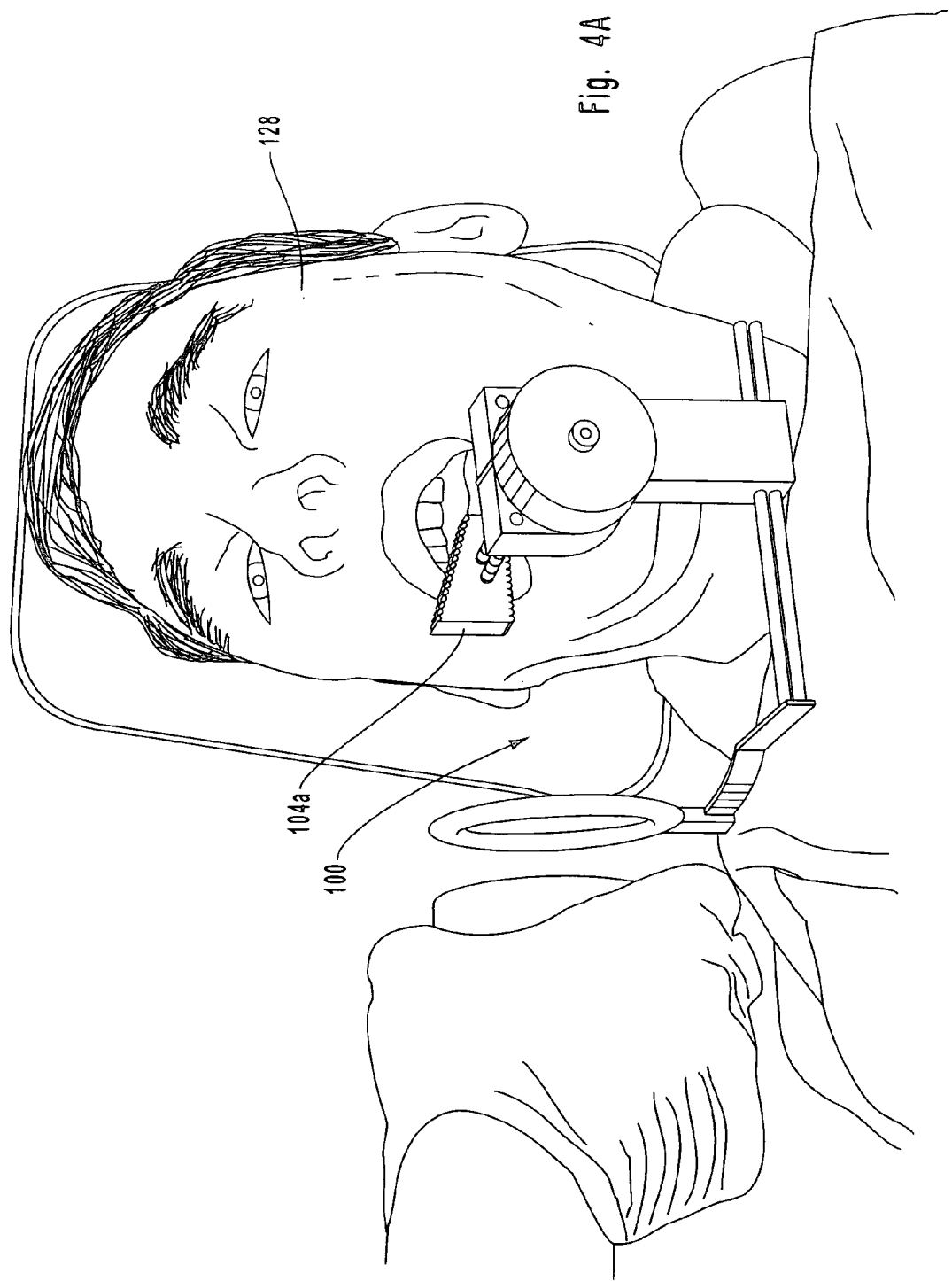

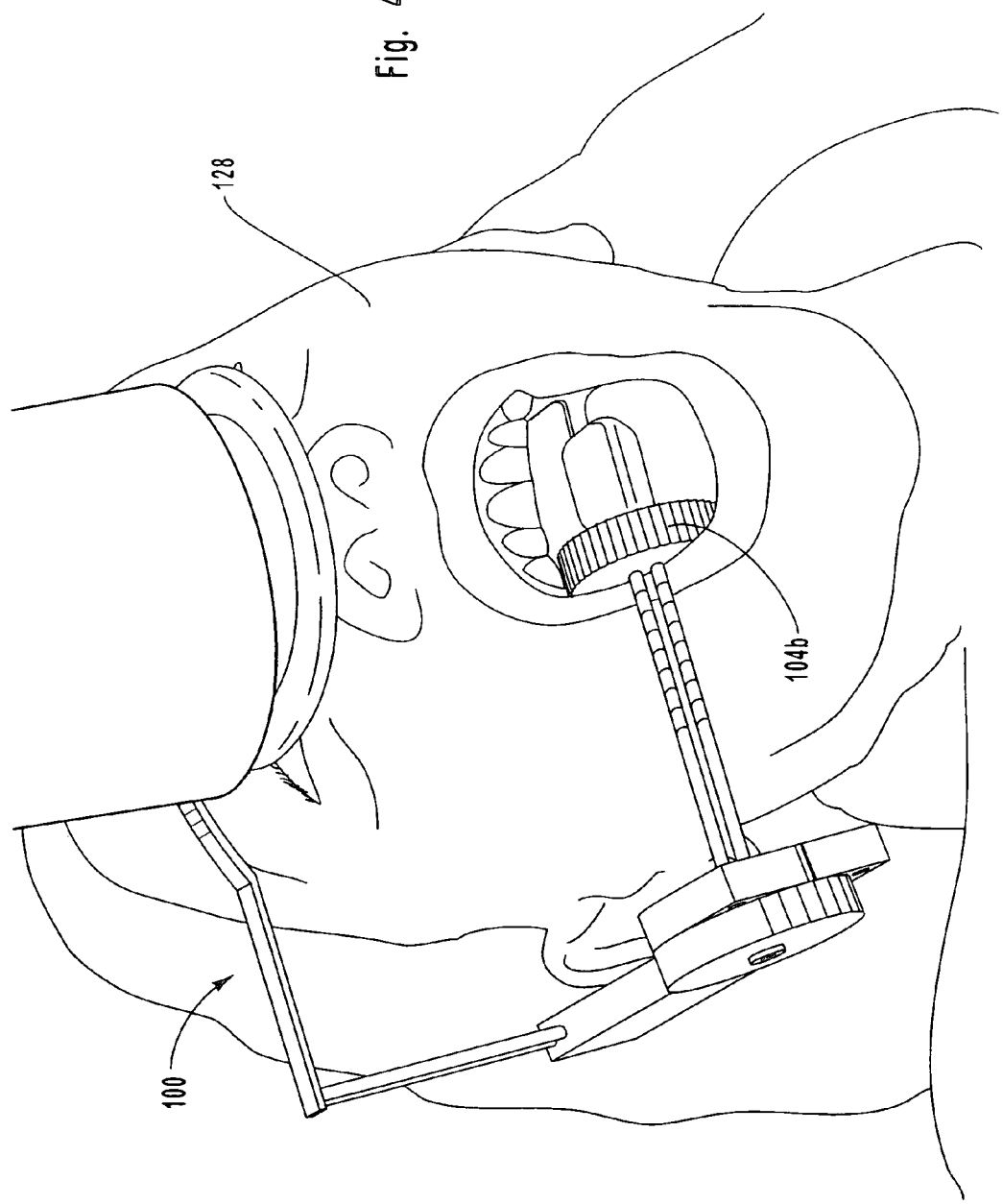

X-RAY POSITIONING DEVICE

BACKGROUND OF THE INVENTION

1. The Field of the Invention

The present invention is in the field of x-ray positioning devices and film holders used to produce radiographs. More particularly, the invention relates to x-ray positioning devices having some degree of adjustability.

2. The Relevant Technology

Dental x-rays are commonly used in the field of dentistry for diagnosis and treatment of the oral cavity. X-rays are able to portray the structural integrity of teeth and supporting tissues if exposed correctly. It is therefore important that x-rays are correctly exposed so as to ensure that a patient receives proper diagnosis and treatment. Proper exposure can be difficult to achieve, however, because of distortions that can occur during exposure.

If an x-ray is not properly positioned when exposed, it can distort or hide the relevant area being radiographed. The inaccurate x-ray can lead to improper diagnosis and treatment by the dental practitioner, which can result in significant harm to the patient by causing a practitioner to wrongfully believe that more or less treatment is needed than actually required.

There are several different dental x-ray techniques that have evolved and been used over the years. One of the oldest techniques requires the patient to hold the x-ray film in place in the patient's mouth with one or more of the patient's fingers. This technique leads to obvious problems because patients might move slightly and therefore cause the x-ray film to be incorrectly positioned. The incorrectly positioned x-ray film also typically results in incorrect angulation, therefore causing distortion of the x-ray. Another serious problem of this technique is that it results in over-exposure of the patient. Because the patient's finger is in his mouth next to the x-ray film, the patient's fingers and hand are unnecessarily exposed to the x-ray radiation.

Alternatively, dental practitioners have used plastic flaps, known as "bite-wings," that are attached to x-ray film packets. Bite wings are flaps that contain adhesive and are capable of attaching to an x-ray film packet. This technique requires the practitioner to attach a bite wing to the back of the x-ray film packet and then place the film packet in the desired location in a patient's mouth. The patient then bites down on the flap and clenches it between the patient's teeth, thereby holding the film packet in the appropriate position.

This technique can also lead to inaccurate x-rays. First, if the practitioner places the bite wing on the film at an incorrect angle, it causes the x-ray to be incorrectly positioned when the patient clenches down on the flap. Also, inaccuracies can easily occur by a patient moving the bite wing with their tongue. Such described instances commonly occur and therefore the use of bite wings sometimes produces inaccurate x-rays.

Another technique and device used to take x-rays is known as Extension Cone Paralleling (XCP). Although XCP may be capable of holding an x-ray film in a patient's mouth, XCP does not allow a dental practitioner to determine the exact angulation of the x-ray, which is important when x-rays are retaken.

In view of the foregoing, there is an ongoing need for improved x-ray positioning devices that are capable of taking x-rays and producing accurate retakes when necessary. Such improvements would lead to more efficient diagnosis and treatment by dental practitioners.

BRIEF SUMMARY OF THE INVENTION

The present invention relates generally to an x-ray positioning device that allows a dental practitioner to adjust the x-ray beam horizontally and vertically relative to the center of the radiographic film with a great degree of precision. The device includes a frame, a bite block connected to the frame, an aiming ring connected to the frame, and an image receptor holder that is also connected to the frame. The aiming ring and image receptor holder are adjustable so as to allow the x-ray beam directed through the aiming ring to be adjustable horizontally and vertically relative to the center of an image receptor (e.g. a radiographic film packet) retained by the image receptor holder.

According to one embodiment, the frame is comprised of a first bar, a second bar, an arm, a first structural member, and a second structural member. One end of the first bar connects the image receptor holder to the frame, while the bite block is also attached to and slidably adjustable along the first bar of the frame. An opposite end of the first bar is connected to the first structural member, which is pivotally attached to a first end of the second structural member. The second bar is attached to the opposite end of the second structural member. The second structural member is attached to the middle portion of the second bar, allowing one end of the second bar to extend unattached, while the opposite end of the second bar is connected to one end of the arm of the frame. The aiming ring is attached to and slidably adjustable near the second end of the arm.

The first bar on which the bite block is slidably adjustable may include markings. According to one embodiment, the markings may comprise indentations. The markings allow precise measurement of the position of the bite block. The bite block may be interchangeable, such that variously configured bite blocks may be interchanged with each other. In addition, the bite block may be formed of a material capable of receiving an impression of a patient's teeth, for example, silicone. The impression of a patient's teeth aids the dental practitioner in configuring the bite block as originally configured when it is necessary to retake x-rays.

The aiming ring is connected to the arm of the frame, and is slidably adjustable along the arm. According to one embodiment, a portion of the arm is curved, with the aiming ring being slidably adjustable along the curved portion of the arm. The aiming ring is configured so as to receive and guide an x-ray tube through which the x-ray beam is directed towards the image receptor.

The image receptor holder may be a unshaped clip, which is attached to the first end of the first bar of the frame. An image receptor, for example, a radiographic film packet, may be inserted and retained within the u-shaped clip of the image receptor holder.

The first bar and image receptor holder form an assembly that is connected to the first structural member of the frame. Because the first structural member is pivotally connected to the second structural member, ultimately, the image receptor may be rotated, as desired. The second structural member includes markings to measure the rotation of the image receptor. Rotation of the image receptor adjusts the vertical positioning so that the x-ray beam directed through the aiming ring meets the image receptor. The markings on the second structural member allow the dental practitioner to measure and record the rotation of the image receptor when it is necessary to retake x-rays.

The combination of the adjustability of the aiming ring (slidable along the arm of the frame), the adjustability of the image receptor (rotatable around the second structural member of the frame), the adjustability of the bite block (slidable along the first bar of the frame), along with the various markings for measuring each adjustment, result in a great degree of overall adjustability and precision when taking and retaking x-rays.

These and other benefits, advantages and features of the present invention will become more full apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which:

FIGS. 4A–4B illustrate exemplary placements of the x-ray positioning device for taking patient x-rays.

DETAILED DESCRIPTION OF THE PREFERRED EMBODIMENTS

I. Introduction

A detailed description of the invention will now be provided with specific reference to figures illustrating preferred embodiments of the invention. It will be appreciated that like structures will be provided with like reference designations. To provide context for interpreting the scope of the invention, certain terms used throughout the application will now be defined.

Figure 1:
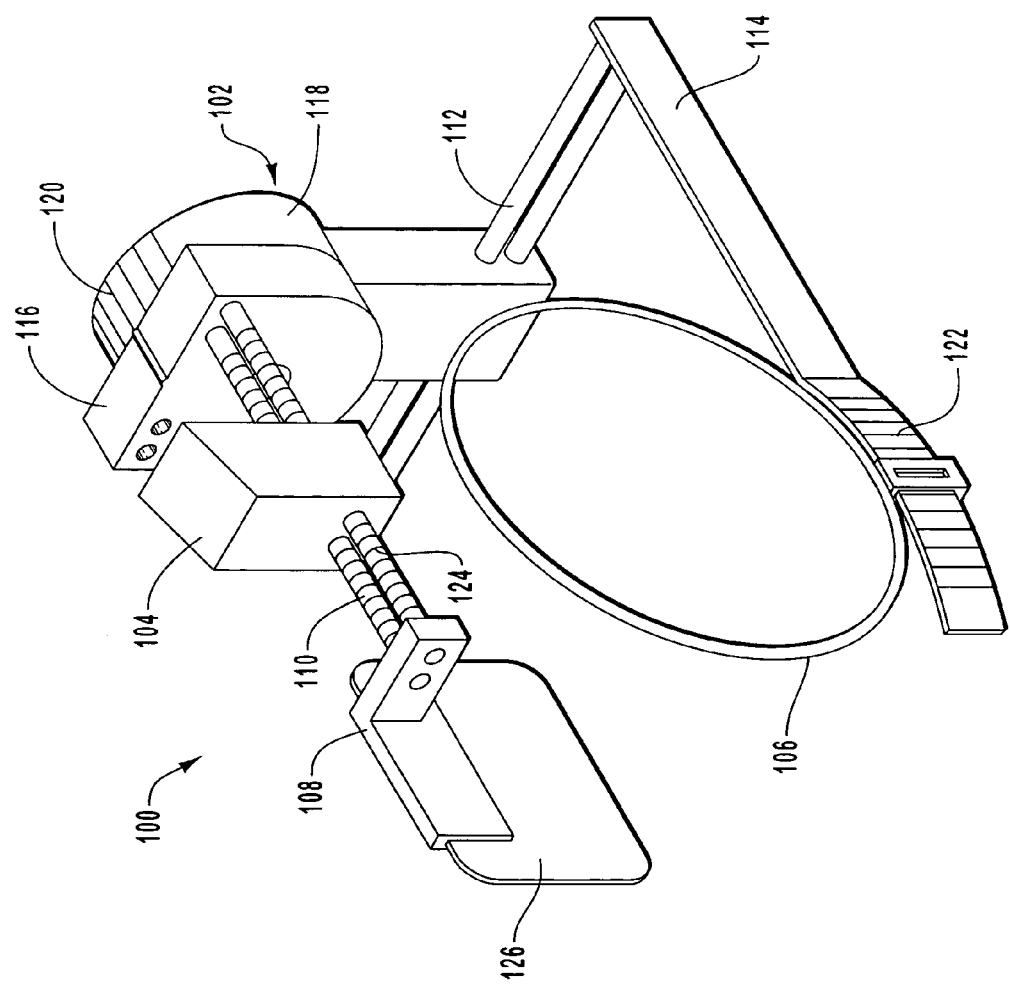
FIG. 1 is a perspective view of an exemplary x-ray positioning device.
Figure 2:
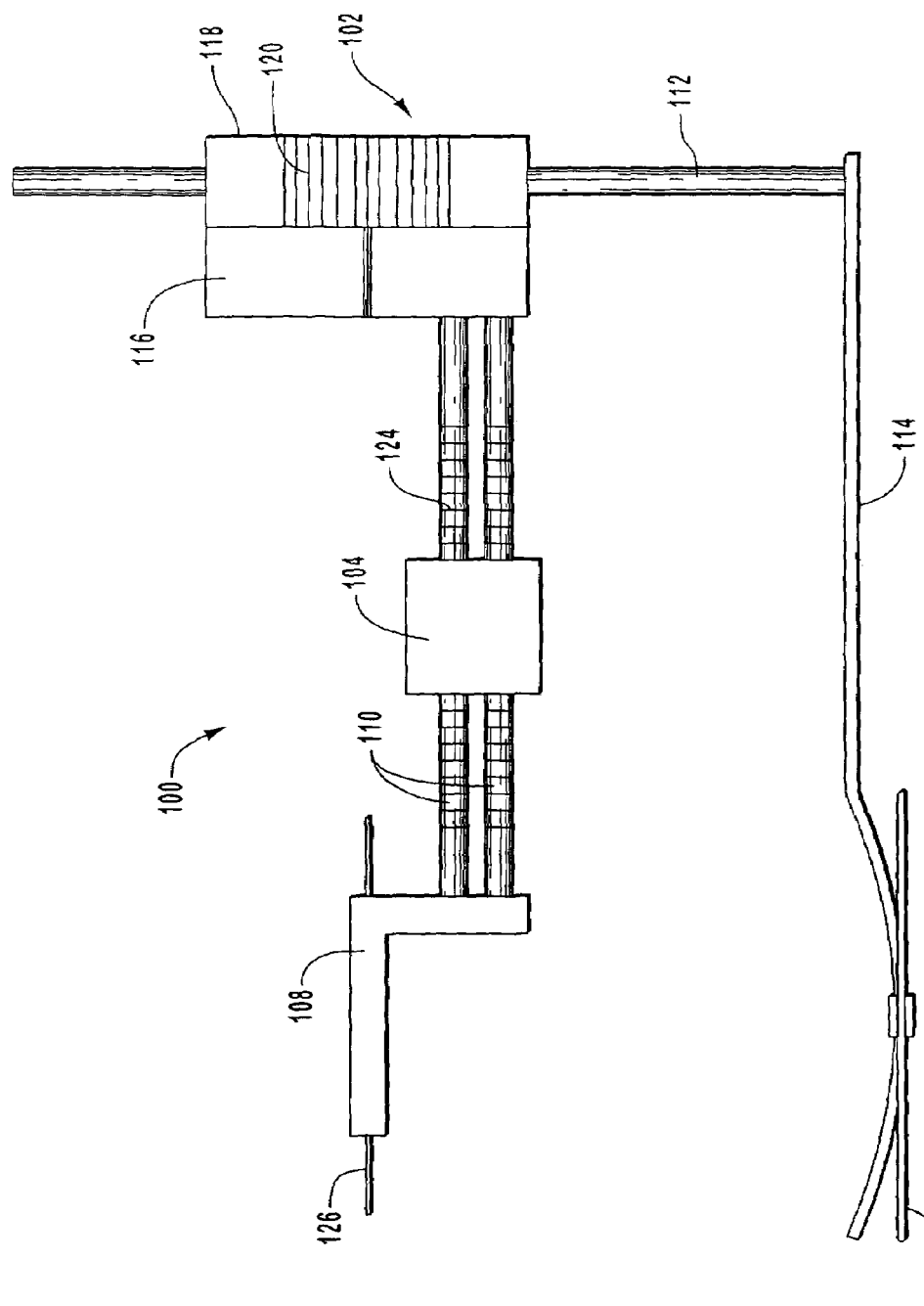
FIG. 2 is a top view of the x-ray positioning device depicted in FIG. 1.

The present invention is directed towards an x-ray positioning device that allows a user to take precise radiographic exposures in all areas of a patient's mouth. The device is designed to allow various components of the x-ray device to be adjustable so that additional x-rays may be precisely repeated in the same location using the same angulations. FIGS. 1 and 2 illustrate an exemplary embodiment of an x-ray positioning device. The device includes a frame, a bite block, an image receptor holder, and an aiming ring.

As used herein, the term "x-ray" includes radiographs and other imaging technologies known and used in the art.

II. Exemplary X-Ray Positioning Device

FIG. 1 is a perspective view of an exemplary x-ray positioning device 100. The device 100 includes a frame 102, a bite block 104, an aiming ring 106, and an image receptor holder 108. X-ray positioning device 100 is designed to be adjustable so as to allow a user to take x-rays in the precise same configuration as earlier x-rays, thereby creating identical repeated radiographs.

A. Frame

Frame 102 is the main supporting structure of x-ray positioning device 100 and is designed to provide support to the other components of the device 100. According to the embodiment illustrated in FIG. 1, frame 102 includes a first bar 110, a second bar 112, an arm 114, a first structural member 116 and a second structural member 118.

In the embodiment illustrated in FIG. 1, the first and second structural members 116 and 118 respectively, may comprise the main supporting structure of the frame 102. Other frame members are attached to these structural members, from which all the components of x-ray positioning device 100 may be supported. The second structural member 118 includes markings 120 so that a user can precisely measure the rotation of the first bar 110 and attached image receptor holder 108. Although the structural members 116 and 118 are depicted in FIG. 1 as being of a particular shape, any suitable shape and configuration may be used.

As illustrated in FIG. 1, first bar 110 is part of the frame structure 102 that supports bite block 104 and image receptor holder 108. One end of first bar 110 connects to first structural member 116 while the opposite end of first bar 110 connects to image receptor holder 108. The first bar 110 may comprise a single piece, or as illustrated, it may comprise a plurality of rods.

The second bar 112 is attached to the second structural member 118. The second structural member 118 is attached to the middle portion of the second bar 112, allowing one end of the second bar 112 to extend unattached, while the opposite end of the second bar 112 is connected to the arm 114.

Arm 114 is part of the frame structure 102, and supports aiming ring 106. One end of arm 114 is connected perpendicularly to second rod 112, while the opposite end extends outward and is configured for receiving the aiming ring 106. As shown in the illustrated embodiment, the free end of arm 114 has a curved portion along which aiming ring 106 can be adjusted. Arm 114 may also contain measurement markings 122 along the curved portion so as to allow a user to record the position of the aiming ring 106 during the x-ray. Markings 122 may also include indentations formed in the arm 114. Indentations allow the aiming ring 106 to more easily remain in the position selected.

B. Bite Block

Bite block 104 is the structure that the patient bites on with his or her teeth, to secure and hold the x-ray positioning device 100 in the appropriate configuration relative to the patient's mouth while x-rays are taken. Bite block 104 is connected to first bar 110 and is slidably adjustable along the bar 110. First bar 110 includes markings 124 to facilitate measuring the position of bite block 104. Markings 124 may also include indentations formed in the bar 110. Indentations allow the bite block 104 to more easily remain in the position selected. Recording this measurement along with which of the patient's teeth contact the bite block 104 allows the bite block 104 to be placed in the same location if additional identical x-rays are to be taken at a later time.

Figure 3B:
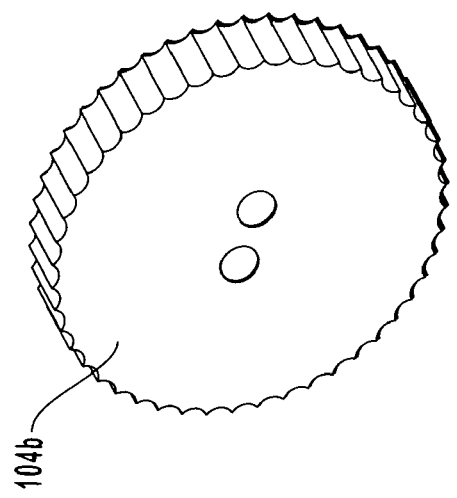
FIGS. 3A–3C illustrate various embodiments of exemplary bite blocks.
Figure 3C:
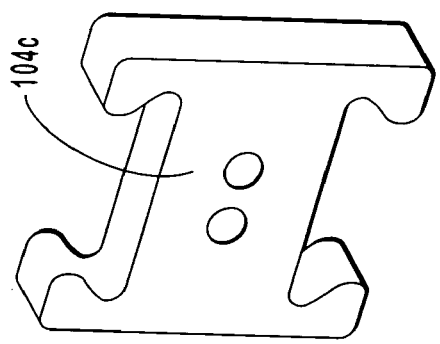
Figure 3A:
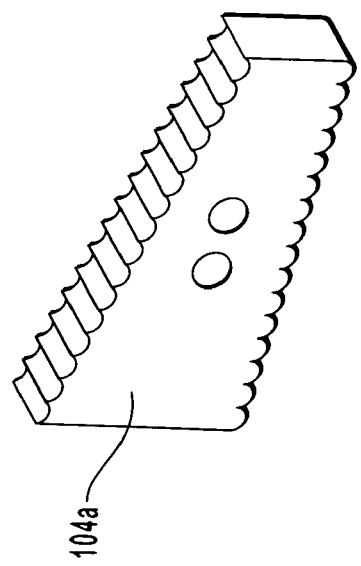

FIGS. 3A–3C illustrate alternative exemplary embodiments of a bite block. FIG. 3A illustrates a trapezoidal bite block 104a. Such a bite block is preferably used in taking x-rays of the molars and biscuspids. FIG. 3B illustrates a circular bite block 104b. Such a bite block is preferably used in taking x-rays of the incisors and canines. FIG. 3C illustrates a third bite block embodiment having an I-beam configuration that is also preferably used in taking x-rays of the molars and bicuspids. According to one embodiment, the bite blocks may be formed of a material capable of receiving and holding an impression of a bite, for example silicone. Such a characteristic more easily facilitates repeated x-rays at a later time.

As will be appreciated by those skilled in the art, other bite block types and configurations can be used without departing from the scope and spirit of the invention. Various shapes, sizes, and materials may be used so long as the bite block is able to be placed in a patient's mouth as intended. Such bite blocks may be specifically configured for use in specific areas of the mouth, configured for use with patients having a small mouth, temporomandibular joint disorder (TMJ), or children's mouths.

The bite block 104 is preferably interchangeable. According to one embodiment, replacement of the bite block 104 may require at least partial disassembly of the remainder of the x-ray positioning device 100, while according to another embodiment the bite block 104 may be removed from the x-ray positioning device 100 without disassembly of the remainder of the device 100.

C. Image Receptor Holder

Image receptor holder 108 is configured to retain an image receptor 126, such as standard x-ray film, a digital x-ray sensor, etc. Image receptor holder 108 is attached to one end of first bar 110. Although the embodiment illustrated in FIG. 1 includes a "clip-like" holder, as will be appreciated by those skilled in the art, a variety of types and configurations of an image receptor holder may be utilized without departing from the scope and spirit of the invention.

D. Aiming Ring

Aiming ring 106 guides the placement of the tube of the x-ray machine. Aiming ring 106 helps align the x-ray tube in the correct position and angulation outside of the patient's mouth so that a proper radiograph can be taken. Aiming ring 106 is connected to arm 114 and is slidably adjustable along the curved portion of arm 114. Because both the aiming ring 106 and the image receptor holder assembly (including image receptor 126, image receptor holder 108, and first bar 110) are independently adjustable, the dental practitioner is able to adjust horizontally and vertically relative to the center of the image receptor 126. Adjustment of the image receptor holder assembly adjusts the incidence of the x-ray source vertically relative to the center of the image receptor 126. Adjustment of the aiming ring 106 adjusts the incidence of the x-ray source horizontally relative to the center of the image receptor 126.

Although aiming ring 106 is depicted in FIG. 1 as being circular, a variety of shapes, such as an oval or polygon, may alternatively be used. For practical purposes, most aiming rings will be shaped according to the shape of the x-ray tube so as to accurately guide the tube to the desired position. However, any shape or configuration may be used as long as the aiming ring is capable of providing accurate guidance to the x-ray tube.

III. Exemplary Method of Use

The x-ray positioning device 100 may be used to take and retake x-rays having the same positioning. In order to use the device 100, the dental practitioner first determines what teeth are to be x-rayed. X-ray positioning device 100 is then placed in the patient's mouth with the patient biting down on bite block 104. Examples of two different configurations are depicted in FIGS. 4A–4B. FIG. 4A illustrates use of device 100 to take an x-ray of a patient's lower molars. Bite block 104a is shown in use in FIG. 4A. FIG. 4B illustrates use of device 100 to take an x-ray of a patient's upper canines and incisors. Bite block 104b is shown in use in FIG. 4B. Once the image receptor 126 and bite block 104a or 104b are properly positioned, the dental practitioner instructs the patient 128 to bite down on bite block 104a or 104b to stabilize the device 100 in the patient's mouth. The dental practitioner is able to record the position of the bite block based on markings 124 located on first bar 110 and which teeth the patient uses to bite down on bite block 104.

By adjusting the orientation of the image receptor holder assembly, the dental practitioner adjusts the incidence of the x-ray source vertically relative to the center of the image receptor 126. Once the desired adjustment has been made, the dental practitioner may record the setting by referring to the markings on the second structural member 118.

The dental practitioner may also adjust the incidence of the x-ray source horizontally relative to the center of the image receptor 126. This is accomplished by adjusting the position of the aiming ring 106 along the curved portion of the arm 114. Once the desired adjustment has been made, the dental practitioner may record the setting by referring to the markings 122 on the arm 114.

It will also be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A dental x-ray positioning device comprising:
   a frame comprised of
      first and second structural members rotatably coupled to one another;
      a first bar connected to said first structural member, said first bar having
         a bite block slidably connected to the first bar, and
         an image receptor holder spaced from the bite block and connected to the first bar; and
      a second bar connected to said second structural member so as to be oriented essentially 90° with respect to the first bar, said second bar having
         an arm attached to said second bar and oriented essentially parallel to said first bar, said arm having an aiming ring slidably connected to the arm; and
   wherein the aiming ring and image receptor holder are adjustable both horizontally and vertically relative to one another so as to allow the center of an x-ray beam directed through the aiming ring to be adjustable horizontally and vertically relative to the center of an image receptor retained by the image receptor holder.

2. A dental x-ray positioning device as defined in claim 1, further comprising an image receptor attached to the image receptor holder.

3. A denial x-ray positioning device as defined in claim 1, wherein the bite block is interchangeable with other variously configured bite blocks.

4. A dental x-ray positioning device as defined in claim 1, wherein the first bar includes markings so as to measure adjustments of the bite block.

5. A dental x-ray positioning device as defined in claim 4, wherein the markings include indentations.

6. A dental x-ray positioning device as defined in claim 1, wherein the arm includes markings so as to measure adjustments of the aiming ring along the arm.

7. A dental x-ray positioning device as defined in claim 1, wherein the markings include indentations.

8. A dental x-ray positioning device as defined in claim 1, wherein the arm includes a curved portion.

9. A dental x-ray positioning device as defined in claims 1 or 8, wherein the second bar comprises a plurality of rods.

10. A dental x-ray positioning device as defined in claim 1, wherein the first bar comprises a plurality of rods.

11. A dental x-ray positioning device as defined in claim 1, wherein the image receptor holder is a u-shaped clip capable of holding said image receptor between the clips.

12. A dental x-ray positioning device as defined in claim 1, wherein the the first structural member has markings so as to measure vertical adjustments of the image receptor holder.

13. A dental x-ray positioning device comprising:

a frame comprised of a first means for slidably positioning a bite block relative to an image receptor holder;

a second means for slidably positioning an aiming ring in an essentially parallel fashion relative to the image receptor; and means for rotatably coupling the first and second means so as that the aiming ring and image receptor holder are vertically adjustable relative to one another so as to allow the center of an x-ray beam directed through the aiming ring to be adjustable horizontally and vertically relative to the center of an image receptor retained by the image receptor holder.

* * * * *